US012602070B2

(12) United States Patent
Sawigun et al.

(10) Patent No.: US 12,602,070 B2
(45) Date of Patent: Apr. 14, 2026

(54) VOLTAGE REFERENCE CIRCUIT AND A POWER MANAGEMENT UNIT

(71) Applicant: IMEC VZW, Leuven (BE)

(72) Inventors: Chutham Sawigun, Leuven (BE); Xiaolin Yang, Leuven (BE)

(73) Assignee: IMEC VZW, Leuven (BE)

( * ) Notice: Subject to any disclaimer, the term of this patent is extended or adjusted under 35 U.S.C. 154(b) by 354 days.

(21) Appl. No.: 18/135,904

(22) Filed: Apr. 18, 2023

(65) Prior Publication Data

US 2023/0333584 A1 Oct. 19, 2023

(30) Foreign Application Priority Data

Apr. 19, 2022 (EP) ..................................... 22168722

(51) Int. Cl.
*G05F 1/595* (2006.01)
*A61B 5/37* (2021.01)
*G05F 1/575* (2006.01)

(52) U.S. Cl.
CPC ............... *G05F 1/595* (2013.01); *A61B 5/37* (2021.01); *G05F 1/575* (2013.01)

(58) Field of Classification Search
CPC . G05F 1/575; G05F 1/56; G05F 1/565; G05F 1/561; G05F 1/468; G05F 1/567; G05F 1/59; G05F 1/46; G05F 1/569; G05F 3/262; G05F 3/242; G05F 3/26; G05F 3/247
See application file for complete search history.

(56) References Cited

U.S. PATENT DOCUMENTS

| | | | |
|---|---|---|---|
| 4,760,284 | A | 7/1988 | Taylor |
| 10,310,537 | B2 | 6/2019 | Dong et al. |
| 2011/0018520 | A1 | 1/2011 | Imura |
| 2011/0128073 | A1* | 6/2011 | Fukuda .................. H10D 84/85 |
| | | | 327/566 |
| 2015/0268689 | A1* | 9/2015 | Blaauw ................... G05F 1/468 |
| | | | 323/313 |

FOREIGN PATENT DOCUMENTS

CN 110167630 A * 8/2019 ............. A61N 1/205

OTHER PUBLICATIONS

CN 110167630 A Translation (Year: 2019).*

(Continued)

*Primary Examiner* — Bryan R Perez
(74) *Attorney, Agent, or Firm* — MOSER TABOADA

(57) ABSTRACT

A voltage reference circuit comprises: first transistor, second transistor, first regulating transistor, and second regulating transistor arranged in a stacked connection, wherein first voltage is provided at first node between first and second transistor, second voltage is provided at second node between second transistor and first regulating transistor, third voltage is provided at third node between first and second regulating transistor; wherein first regulating transistor and second regulating transistor are connected to first node and second node, respectively, for compensating changes in first voltage and second voltage, respectively, to maintain stable voltage levels; wherein voltage reference circuit outputs at least one of the first, second or third voltage as a reference voltage.

18 Claims, 9 Drawing Sheets

(56) References Cited

OTHER PUBLICATIONS

Seok, et al: "A Portable 2-Transistor Picowatt Temperature-Compensated Voltage Reference Operating at 0.5 V", IEEE Journal of Solid-State Circuits, vol. 47, No. 10, pp. 2534-2545, 2012.

Lee, et al: "A Subthreshold Voltage Reference With Scalable Output Voltage for Low-Power IoT Systems", IEEE Journal of Solid-State Circuits, vol. 52, No. 5, pp. 1443-1449, 2017.

Dong, et al: "A 114-pW PMOS-Only, Trim-Free Voltage Reference with 0.26% within-Wafer Inaccuracy for nW Systems", 2016 Symposium on VLSI Circuits Digest of Technical Papers, pp. 1-2, 2016.

Extended European Search Report in EP22168722.1 dated Oct. 14, 2022.

* cited by examiner

VOLTAGE REFERENCE CIRCUIT AND A POWER MANAGEMENT UNIT

CROSS-REFERENCE TO RELATED APPLICATIONS

The present application claims the benefit of and priority to EP Patent Application Serial No. 22168722.1, filed Apr. 19, 2022, the entire contents of which is incorporated herein by reference.

TECHNICAL FIELD

The present description relates to a voltage reference circuit which is configured to generate a reference voltage. The present description further relates to a power management unit comprising the voltage reference circuit.

BACKGROUND

Voltage reference circuits are used for providing a reliable reference voltage, which may further be used to control electronic circuits. For instance, a power management unit typically uses a voltage reference circuit in order to provide a reliable reference voltage, which can be used to generate direct current (DC) voltages and currents for biasing or supplying to an electronic circuit.

The reference voltage output by the voltage reference circuit should provide a stable voltage level which is not affected or minimally affected by parameter variations, such as temperature variations or variations in supply voltage to the reference voltage circuit.

In addition, the voltage reference circuit should be able to consume very small power levels. In particular, the voltage reference circuit may be used in small devices, such as Internet of Things (IoT) devices that may be almost exclusively in a sleep mode and only awake for brief moments of time. Thus, power consumption of such devices is mainly based on the power consumed during sleep mode. The voltage reference circuit may however be always-on and therefore the power consumption of the voltage reference circuit may be of huge importance.

Voltage reference circuits operating in a subthreshold region of transistors may provide a low power consumption. However, the reference voltages output by such voltage reference circuits may be quite low. Therefore, it may be desired to provide a scalable output voltage.

In Lee et al: "*A Subthreshold Voltage Reference With Scalable Output Voltage for Low-Power IoT Systems*", IEEE Journal of Solid-State Circuits, Vol. 52, No. 5, 2017, pp. 1443-1449, a voltage reference circuit is described for providing a relatively large output reference voltage. The voltage reference circuit has four stacked p-type metal-oxide-semiconductor (pMOS) transistors. However, each stacked pMOS transistor provides an increase of reference voltage while producing additional noise and consuming additional power. Hence, the output reference voltage is very sensitive to variations in supply voltage to the voltage reference circuit.

SUMMARY

An objective of the present description is to provide a voltage reference circuit with a possibility to provide a relatively high output reference voltage with a low power consumption and an insensitivity to parameter variations, such as variations in supply voltage and/or temperature.

This and other objectives are at least partly met by the invention as defined in the independent claims. Preferred embodiments are set out in the dependent claims.

According to a first aspect, there is provided a voltage reference circuit comprising: a first transistor comprising a gate terminal, a source terminal, and a drain terminal; a second transistor comprising a gate terminal, a source terminal, and a drain terminal, wherein the first transistor and the second transistor are arranged in a stacked connection between a terminal connected to ground and a terminal connected to a supply voltage, wherein a first voltage is provided at a first node between the first transistor and the second transistor; a first regulating transistor comprising a gate terminal, a source terminal, and a drain terminal, wherein the first regulating transistor is connected between the supply voltage and the first transistor in a stacked connection with the second transistor, wherein a second voltage is provided at a second node between the second transistor and the first regulating transistor, and wherein the first regulating transistor is connected to the first node for compensating changes in the first voltage at the first node to maintain a stable first voltage level; and a second regulating transistor comprising a gate terminal, a source terminal, and a drain terminal, wherein the second regulating transistor is connected between the supply voltage and the second transistor in a stacked connection with the first regulating transistor, wherein a third voltage is provided at a third node between the first regulating transistor and the second regulating transistor, and wherein the second regulating transistor is connected to the second node for compensating changes in the second voltage at the second node to maintain a stable second voltage level; wherein the voltage reference circuit is configured to output at least one of the first voltage, the second voltage, or the third voltage as a reference voltage.

According to the first aspect, a first regulating transistor and a second regulating transistor are added to a voltage reference circuit having a first transistor and a second transistor. The first regulating transistor and the second regulating transistor are configured to provide compensation for any changes in a voltage level at the first node and second node, respectively. This implies that the regulating transistors are configured to ensure that a stable reference voltage may be output such that even though the regulating transistors may slightly add to power consumption of the voltage reference circuit, the regulating transistors are useful in enabling output of a reference voltage that is insensitive to parameter variations, such as temperature variations or variations in supply voltage to the reference voltage circuit.

Further, since the regulating transistors are arranged in a stacked connection with the first and second transistors, the second voltage at the second node is larger than the first voltage at the first node (as there are two transistors stacked between ground and second node compared to only the first transistor being arranged between ground and the first node). Similarly, the third voltage at the third node is larger than the second voltage at the second node. Thus, the voltage reference circuit enables scaling of a reference voltage compared to using only the first and the second transistor in the voltage reference circuit.

The voltage reference circuit may be used for outputting any one of the first voltage, the second voltage, or the third voltage as the reference voltage. The first voltage has a very low sensitivity to parameter variations, since the first voltage level is affected by two rounds of regulation, via the first regulating transistor and the second regulating transistor. The second voltage is larger than the first voltage and is also insensitive to parameter variations, thanks to the regulation provided by the second regulating transistor. The third voltage is even larger than the second voltage but may not be as insensitive to parameter variations.

Thus, if it is desired that the output reference voltage should have very low sensitivity to parameter variations, the voltage reference circuit may be set up to output the first voltage as the reference voltage. If it is desired that a relatively large reference voltage is to be provided with still low sensitivity to parameter variations, the voltage reference circuit may be set up to output the second voltage as the reference voltage. If it is desired that a large reference voltage is provided, the voltage reference circuit may be set up to output the third voltage as the reference voltage.

The voltage reference circuit may thus be utilized in different manners depending on desired properties of the reference voltage. Also, the voltage reference circuit may be configured to output more than one reference voltage. Thus, the voltage reference circuit may provide more than one level of reference voltage.

The definition that transistors are arranged in a stacked connection should be understood such that the transistors are connected in series for providing a common direction of current through the transistors in the voltage reference circuit. Thus, a current between drain and source through one transistor may continue between drain and source of the other transistor in the stacked connection. In other words, if the transistors are of same type, the transistors may be connected with drain of one transistor in the stacked connection connected to source of the other transistor in the stacked connection. If the transistors are of opposite type, the transistors may be connected with source of one transistor connected with source of the other transistor in the stacked connection.

Further, the transistors being arranged in stacked connection between two terminals (e.g., first transistor and second transistor are arranged in stacked connection between a terminal connected to ground and a terminal connected to supply voltage) implies that drain or source of one transistor is connected to one of the two terminals and drain or source of the other transistor is connected to the other of the two terminals.

As used herein, the term "connected" should be construed as comprising directly connected, such that no components are arranged between the terminals/devices that are connected unless stated otherwise. The stacked connection of transistors being described in relation to the supply voltage does however not necessarily mean that the transistor is directly connected to the supply voltage. Rather, further transistors may be stacked between the supply voltage and the transistors of the described stacked connection. For instance, at least the second regulating transistor is arranged between the supply voltage and the first regulating transistor. Similarly, additional regulating transistor(s) may be arranged between the supply voltage and the second regulating transistor and/or may be arranged between the first regulating transistor and the second regulating transistor. This also implies that the third node need not be directly connected to the first regulating transistor and the second regulating transistor. Rather, the third node may be arranged between any two regulating transistors in a stack if the voltage reference circuit comprises more than two regulating transistors. This may also imply that the third voltage at the third node may in fact be regulated by being connected to an additional regulating transistor for compensating changes in the third voltage.

The first regulating transistor is connected in a stacked connection with the second transistor, the second transistor being between the first regulating transistor and the first node. The first regulating transistor is further connected to the first node for compensating changes in the first voltage. The first regulating transistor may thus receive feedback from the first node such that any changes in the first voltage may affect the regulating transistor and may be compensated for by the first regulating transistor via the second transistor back to the first node. Thus, the first regulating transistor may be connected to the first node by the gate terminal of the first regulating transistor being connected to the first node or by a bulk terminal (if available) of the first regulating transistor being connected to the first node. Similarly, the second regulating transistor may be connected to the second node by the gate terminal of the second regulating transistor being connected to the second node or by a bulk terminal (if available) of the second regulating transistor being connected to the second node.

According to an embodiment, the voltage reference circuit further comprises at least one additional regulating transistor, wherein each of the at least one additional regulating transistor is connected to another regulating transistor in a same manner as the second regulating transistor is connected to the first regulating transistor.

This may be used for further scaling a reference voltage output by the voltage reference circuit. It may also or alternatively be used for providing further rounds of regulation of the voltage levels.

Thus, the first regulating transistor, the second regulating transistor and the additional regulating transistors form a stack between the supply voltage and the second transistor. Also, an additional node is provided between each pair of regulating transistors in the stack. The voltage at such additional node may be output as additional reference voltage. Further, the additional node is also connected to the regulating transistor arranged immediately above the pair of regulating transistors in the stack for compensating changes in the voltage at the additional node.

For example, if the voltage reference circuit comprises a third regulating transistor, the third regulating transistor is connected between the supply voltage and the first regulating transistor in a stacked connection with the second regulating transistor. The first, second, and third regulating transistors thus form a stack between the second transistor and the supply voltage. Further, the third node is between the pair of the first regulating transistor and the second regulating transistor, and the third node is also connected to the third regulating transistor arranged immediately above the pair of the first and second regulating transistors in the stack for compensating changes in the voltage at the third node.

According to an embodiment, the first transistor, the second transistor, the first regulating transistor, and the second regulating transistor are all n-type metal-oxide-semiconductor (nMOS) transistors, and wherein a drain terminal of the first transistor is connected to a source terminal of the second transistor, a drain terminal of the second transistor is connected to a source terminal of the first regulating transistor and a drain terminal of the first regulating transistor is connected to a source terminal of the second regulating transistor, and wherein the first node is connected to the drain terminal of the first transistor and the source terminal of the second transistor, the second node is connected to the drain terminal of the second transistor and the source terminal of the first regulating transistor, and the third node is connected to the drain terminal of the first regulating transistor and the source terminal of the second regulating transistor.

It should however be realized that the first transistor may be a pMOS transistor instead in combination the second transistor and the regulating transistors being nMOS transistors. In such case, a source terminal of the first transistor may be connected to the source terminal of the second transistor and the first node may be connected to the source terminal of the first transistor.

The drain terminal of the second transistor may thus be connected to the source terminal of the first regulating transistor. Further, the source terminal of the second transistor is connected to the first node, which is further connected to, for example, the gate terminal of the first regulating transistor (it should be realized that the first node may alternatively be connected to a bulk terminal of the first regulating transistor). This implies that the drain-to-source voltage of the second transistor ($V_{DS2}$) is equal to a negative of the gate-to-source voltage of the first regulating transistor ($V_{GS3}$), i.e., $V_{DS2}=-V_{GS3}$. Thus, any fluctuation in parameters, such as change in temperature or supply voltage, causing $V_{DS2}$ to change will result in the change being sensed by the gate-to-source voltage of the first regulating transistor $V_{GS3}$ and being directly fed back to change $V_{DS2}$ in an opposite direction. Thus, drain current of the second transistor will change to bring the first voltage at the first node back to an original value. Hence, a stable first voltage level is maintained.

It should be realized that at least the second voltage at the second node may be regulated in a corresponding manner using the second regulating transistor such that a stable second voltage level is also maintained.

According to an embodiment, an aspect ratio of the first regulating transistor equals an aspect ratio of the second transistor.

This may imply that the circuit is easy to manufacture as the transistors may be identical.

Further, the behavior of the second transistor and the first regulating transistor may be identical based on having the same aspect ratios. With equal drain currents flowing through the second transistor and the first regulating transistor, voltage levels may be easily controlled when the aspect ratio is equal. Also, when the second transistor and the first regulating transistor have the same aspect ratio, the second voltage at the second node may be two times larger than the first voltage at the first node. This implies that the voltage level is substantially increased between the first node and the second node.

The aspect ratio may be defined as a width of a channel of the transistor divided by a length of the channel.

When additional regulating transistors are present such that the stack of regulating transistors is formed between the supply voltage and the second transistor, all of the regulating transistors may have the same aspect ratio as the second transistor. This may facilitate control of voltage levels of the voltage reference circuit and also it may ensure that the voltage level is scaled by an equal amount between adjacent nodes in the voltage reference circuit (difference between third and second voltage is equal to difference between second and first voltage, and so on).

The topmost regulating transistor in the stack of regulating transistors, which is directly connected to the supply voltage, may have a different aspect ratio than the other regulating transistors in the stack. The topmost regulating transistor may be sized slightly differently to compensate for non-idealities in the voltage reference circuit. If there are only two regulating transistors, the second regulating transistor may thus be differently sized compared to the first regulating transistor.

According to an embodiment, the voltage reference circuit is configured to output a reference voltage from a node having a largest voltage and being regulated by a regulating transistor.

When a node is regulated by a regulating transistor, the voltage level output at the node will be maintained at a stable level. Thus, by outputting the reference voltage from the node having the largest voltage and being regulated, a large reference voltage is provided while also a stable level of the reference voltage is provided.

If the voltage reference circuit comprises only the first and the second regulating transistors, the third node is not regulated by any regulating transistor (because the third node is not connected to any regulating transistor for compensating changes in the third voltage). Thus, in such case, the voltage reference circuit outputting a reference voltage from a node having a largest voltage and being regulated by a regulating transistor would be configured to output the reference voltage from the second node.

A top node between the topmost regulating transistor in the stack and the regulating transistor directly connected to the topmost regulating transistor will not be regulated. Thus, even though this top node provides a larger voltage than the node having largest regulated voltage, the voltage reference circuit may preferably not use this top node for providing the reference voltage since the voltage level at this top node may be sensitive to parameter variations. However, it should be realized that the voltage level at the top node may still be relatively insensitive to parameter variations and that in some embodiments it may still be useful for output of the reference voltage.

The node between the pair of regulating transistors closest to the topmost regulating transistor will be the node having the largest voltage and being regulated by a regulating transistor (being regulated by the topmost regulating transistor).

According to another embodiment, the voltage reference circuit is configured to output a reference voltage from the first node.

Even though the first voltage at the first node is smaller than the voltages at other nodes (second node, third node, etc.), it may still be desired in some embodiments that the voltage reference circuit outputs the first voltage as the reference voltage. The first voltage may be very well regulated based on a multitude of regulating transistors affecting the voltage level at the first node. This implies that the first voltage may be very insensitive to parameter variations. Thus, if having a reference voltage which is stable is of utmost importance, the first node may be used for output of the reference voltage.

According to an embodiment, the voltage reference circuit is configured to output more than one reference voltage.

Thus, the voltage reference circuit may output voltage from more than one of the first to third nodes (and also from additional nodes). This may be useful when several different levels of voltages are needed in an electronic circuit.

Further, the voltage level is scaled by an equal amount between adjacent nodes in the voltage reference circuit (difference between third and second voltage is equal to difference between second and first voltage, and so on). Thus, when a plurality of reference voltages is output, each of the reference voltages may be defined by an integer number times the first voltage.

For instance, the voltage reference circuit may provide reference voltages that may be used by a successive approximation register analog-to-digital converter, in which a sampled value is compared to a plurality of different levels in order to digitize the sampled value.

According to an embodiment, each of the first transistor, the second transistor, the first regulating transistor and the second regulating transistor further comprises a bulk terminal, and wherein the first node is connected to the bulk terminal of the first regulating transistor, and the second node is connected to the bulk terminal of the second regulating transistor.

This may facilitate implementation of the voltage reference circuit in technology in which bulk terminal of transistors is available, such as in fully-depleted silicon-on-insulator (FD-SOI) technology.

Also, it should be realized that the first terminal need not use a bulk terminal. Thus, even though the second transistor, the first regulating transistor and the second regulating transistor may comprise a bulk terminal, the first terminal need not do so.

It should be realized that although conventional complementary metal-oxide-semiconductor (CMOS) technology may not provide a bulk terminal providing an extra gate terminal for individually controlling transistors, the voltage reference circuit may be implemented in CMOS technology. For instance, the second transistor, the first regulating transistor, and the second regulating transistor may be implemented as nMOS transistors associated with deep n-wells for providing bulk terminals of the nMOS transistors.

Thanks to the first node being connected to the bulk terminal of the first regulating transistor, the first regulating transistor receives feedback from the first node on its bulk terminal. This implies that any change in the first voltage affects the bulk terminal of the first regulating transistor such that the first voltage can be maintained at a stable, unchanged first voltage level. In the same way, the second regulating transistor receives feedback from the second node on its bulk terminal such that the second voltage can be maintained at a stable, unchanged second voltage level.

By connecting the first and second nodes to bulk terminals of the first and second regulating transistors, respectively, body effect of the regulating transistors is utilized for maintaining stable voltage levels. This implies that losses due to body effects in scaling of the voltage between different nodes may be avoided.

The gate terminal of the first regulating transistor may be connected to the source terminal of the first regulating transistor.

The gate terminal of the second regulating transistor may be connected to the source terminal of the second regulating transistor.

By having the gate terminal connected to the source terminal, a gate-to-source voltage of the transistor is zero (as the gate and source terminals are connected). Hence, drain current of the first regulating transistor and the second regulating transistor may be controlled only by bulk-to-source voltage of the respective regulating transistor.

The gate terminal of the second transistor may be connected to the source terminal of the second transistor.

This implies that a gate-to-source voltage of the second transistor $V_{GS2}$ is zero (as the gate and source terminals are connected). Hence, drain current of the second transistor may be controlled only by bulk-to-source voltage of the second transistor $V_{BS2}$.

The bulk terminal of the second transistor may be connected to ground.

This implies that the bulk-to-source voltage of the second transistor $V_{BS2}$ is negative, since the source terminal is connected to the first node. In particular, the bulk-to-source voltage of the second transistor $V_{BS2}$ is a negative of the first voltage.

The second transistor may be configured to operate in saturation at a subthreshold region. If a drain-to-source voltage of the second transistor $V_{DS2}$ is larger than $4*V_T$ (where $V_T$ is thermal voltage), drain current of the second transistor is controlled only by the negative bulk-to-source voltage of the second transistor $V_{BS2}$. This implies that an extremely low drain current of the second transistor is generated. Hence, the voltage reference circuit may consume ultra-low power.

Further, since the gate-to-source voltage of the second transistor $V_{GS2}$ is zero and the bulk-to-source voltage of the second transistor $V_{BS2}$ is also constant (thanks to the bulk-to-source voltage being the negative of the reference voltage, which is maintained constant), the drain current of the second transistor is constant if the drain-to-source voltage is constant. With the drain-to-source voltage of the second transistor $V_{DS2}$ being equal to a negative of the bulk-to-source voltage of the first regulating transistor $V_{BS3}$, the feedback from the first regulating transistor may be used for maintaining the drain-to-source voltage of the second transistor $V_{DS2}$ constant and ensuring that a constant drain current of the second transistor is provided.

The bulk terminal of the first transistor may be connected to ground.

The bulk and source terminals of the first transistor may further be connected and the drain and gate terminals of the first transistor may also be connected and connected to the first node. This implies that the first voltage at the first node corresponds to a gate-to-source voltage of the first transistor $V_{GS1}$.

According to an alternative, the gate terminal of the first transistor is connected to ground.

The gate and source terminals of the first transistor may further be connected to each other and the drain and bulk terminals of the first transistor may also be connected to each other and connected to the first node. This implies that the first voltage at the first node corresponds to a bulk-to-source voltage of the first transistor $V_{BS1}$.

This may be used for ensuring that the first voltage at the first node is insensitive to parameter variations. However, the scaling of the first voltage to the second voltage will not be as large (two times the first voltage) compared to when the bulk terminal of the first transistor is connected to ground as described above.

According to an embodiment, the first transistor, the second transistor, the first regulating transistor and the second regulating transistor are input/output transistors.

An integrated circuit may comprise input/output transistors and core transistors. Core transistors may have a relatively thin gate oxide layer and are typically used for high speed operations which may be used internally in the integrated circuit. In comparison to core transistors, input/output transistors may have a relatively thick gate oxide layer and are typically used for communication with external devices and, hence, the transistors may be referred to as input/output transistors but could also be referred to as thick oxide transistors. Thus, the first transistor, the second transistor, the first regulating transistor and the second regulating transistor being input/output transistors should be construed as the transistors being a particular type of transistor within an integrated circuit rather than the transistors necessarily being arranged to communicate with any external device.

The input/output transistors have a low gate leakage current. This implies that the gate leakage current may be negligible compared to drain current of the transistors. The first transistor, the second transistor, the first regulating transistor and the second regulating transistor may further be connected such that an equal drain current is provided through all the transistors. This implies that the current through the transistors may be accurately controlled for ensuring that a stable reference voltage is maintained.

According to an embodiment, the first node is connected to the gate terminal of the first regulating transistor, and the second node is connected to the gate terminal of the second regulating transistor.

Thus, instead of connecting the first and second nodes to bulk terminals of the first and second regulating transistors, respectively, the first and second nodes may be connected to gate terminals of the first and second regulating transistors, respectively.

This implies that the transistors in the voltage reference circuit need not provide a possibility to connect to a bulk terminal. This may facilitate implementing the voltage reference circuit in bulk CMOS technology.

According to an embodiment, the gate terminal of the first transistor is connected to the first node.

The source terminal of the first transistor may further be connected to ground and the drain terminal of the first transistor may also be connected to the first node. This implies that the first voltage at the first node corresponds to a gate-to-source voltage of the first transistor $V_{GS1}$.

According to an embodiment, the gate terminal of the second transistor is connected to ground.

This implies that the gate-to-source voltage of the second transistor $V_{GS2}$ is negative since the source terminal is connected to the first node. In particular, the gate-to-source voltage of the second transistor $V_{SB2}$ is a negative of the first voltage.

The second transistor may be configured to operate in saturation at a subthreshold region. If a drain-to-source voltage of the second transistor $V_{DS2}$ is larger than $4*V_T$ (where $V_T$ is thermal voltage), drain current of the second transistor is controlled only by the negative gate-to-source voltage of the second transistor $V_{BS2}$. This implies that an extremely low drain current of the second transistor is generated. Hence, the voltage reference circuit may consume ultra-low power.

According to an embodiment, the first transistor is an input/output transistor and wherein each of the second transistor, the first regulating transistor and the second regulating transistor is a native transistor, an oxide layer of the native transistor being thinner than an oxide layer of the input/output transistor.

A native transistor can be formed without specially grown oxide, using only a natural thin oxide film that may be formed over silicon during processing of other layers when manufacturing transistors. Such native transistors are available in bulk CMOS technology and may be used in the voltage reference circuit in order to provide low power consumption and provide that the native transistors operate in saturation at a subthreshold region for a negative gate-to-source voltage.

The first transistor has a thicker oxide layer than the second transistor and the first and second regulating transistors. This implies that the first transistor also has a higher threshold voltage than the second transistor and the first and second regulating transistors.

In comparison, when the first and second nodes are connected to bulk terminals of the first and second regulating transistors, respectively, no native transistors need to be used. Further, using input/output transistors for the second transistor and the regulating transistor compared to using native transistors implies that an improved temperature insensitivity is provided. Native transistors sharing the same substrate imply that parasitic p-n junction diodes are formed between the substrate and the source terminals of the native transistors. At high temperatures, significant reverse-biased leakage current may occur which may affect the output reference voltage. However, using input/output transistors with separate bulk terminals such leakage current may be avoided.

On the other hand, for bulk CMOS technology, bulk terminals may not be available. Hence, in such case, native transistors may still be used for implementing the voltage reference circuit in bulk CMOS technology.

According to a second aspect, there is provided a power management unit comprising the voltage reference circuit according to the first aspect, the power management unit being configured to produce a direct current (DC) voltage based on the reference voltage.

Effects and features of this second aspect are largely analogous to those described above in connection with the first aspect. Embodiments mentioned in relation to the second aspect are largely compatible with the first aspect.

Power management units typically provide DC voltages and currents for supplying to an electronic circuit. Thanks to the voltage reference circuit providing a stable reference voltage level, the power management unit may also provide reliable supply voltages to electronic circuits connected to the power management unit.

Further, the voltage reference circuit may provide a low power consumption such that the power management unit may also be provided with low power consumption.

The solutions described in the present description can be applied in numerous electronic circuitry devices and applications.

According to a third aspect, there is provided a neural sensing apparatus comprising the power management unit according to the second aspect.

Effects and features of this third aspect are largely analogous to those described above in connection with the first and second aspects. Embodiments mentioned in relation to the third aspect are largely compatible with the first and second aspects.

For a neural sensing apparatus, such as a neural probe, it is particularly advantageous if the apparatus is small, stable and/or power efficient. Thus, the power management unit utilizing the voltage reference circuit may be particularly advantageous to use in the neural sensing apparatus.

BRIEF DESCRIPTION OF THE DRAWINGS

The above, as well as additional objects, features, and advantages of the present inventive concept, will be better understood through the following illustrative and non-limiting detailed description, with reference to the appended drawings. In the drawings like reference numerals will be used for like elements unless stated otherwise.

DETAILED DESCRIPTION

Figure 1:
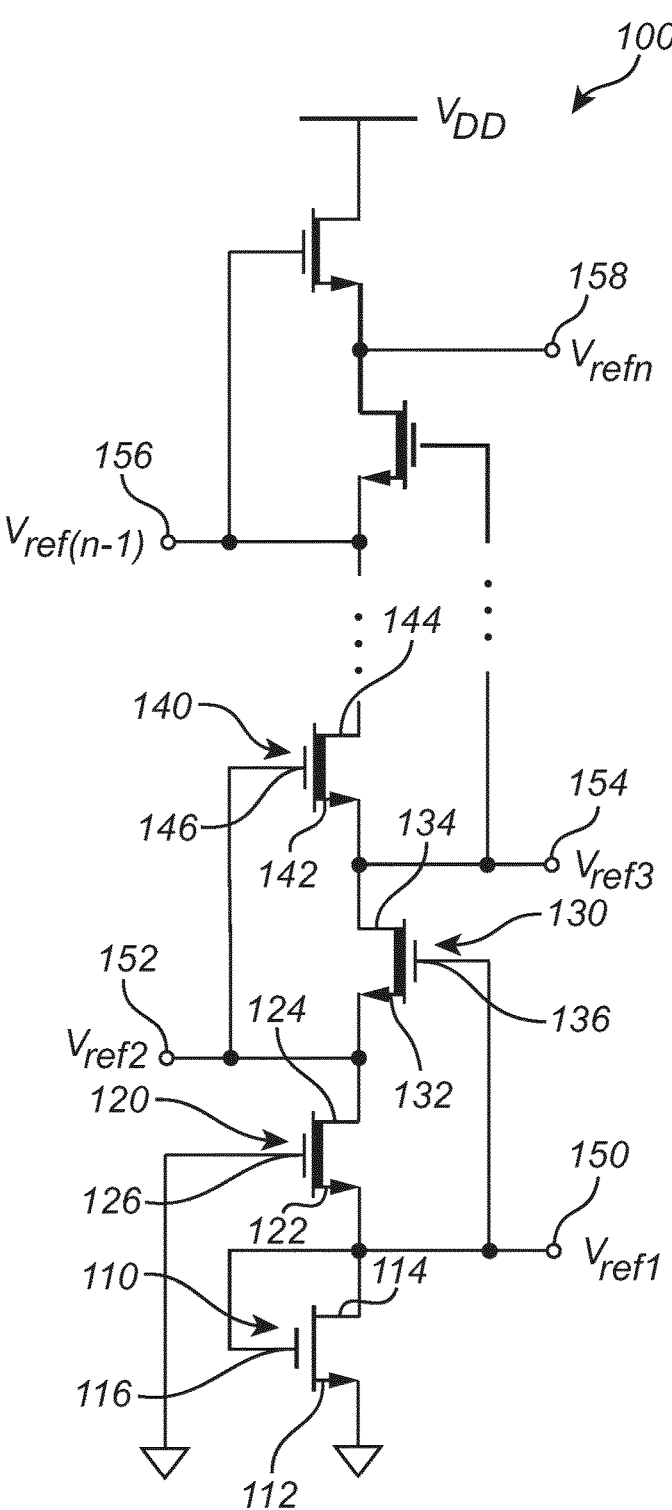
FIGS. 1-2 are schematic views of a voltage reference circuit according to a first embodiment.
Figure 2:
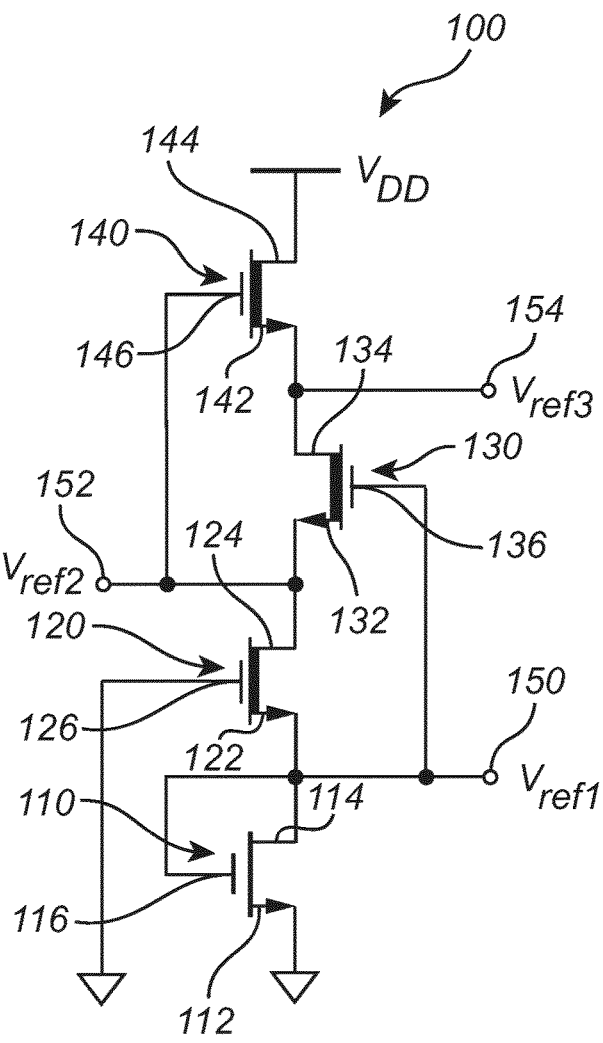

Referring now to FIGS. 1 and 2, a voltage reference circuit 100 according to a first embodiment will be described. The voltage reference circuit 100 comprises a first transistor 110, a second transistor 120 and at least a first regulating transistor 130 and a second regulating transistor 140. As illustrated in FIG. 1, the voltage reference circuit 100 may comprise a large number of regulating transistors and, as illustrated in FIG. 2, the voltage reference circuit 100 may comprise only the first regulating transistor 130 and the second regulating transistor 140.

Each of the first transistor 110, the second transistor 120 and the regulating transistors 130, 140 may be a n-type metal-oxide-semiconductor (nMOS) transistor and the description below is based on the transistors being nMOS transistors. However, it should be realized that the first transistor 110 may instead be a p-type metal-oxide-semiconductor (pMOS) transistor. In such case, source and drain terminals of the transistor should switch places with each other.

The second transistor 120 and the regulating transistors 130, 140 may be configured to have a very low threshold voltage. Thus, the second transistor 120 and the regulating transistors 130, 140 may advantageously be native transistors. A native transistor can be formed without specially grown oxide, using only a natural thin oxide film that may be formed over silicon during processing of other layers when manufacturing transistors.

Thus, the voltage reference circuit 100 may be particularly suited for implementation using technology for which native transistors are available. Hence, the voltage reference circuit 100 may for instance be formed using bulk complementary metal-oxide-semiconductor (CMOS) technology.

Each of the first transistor 110, the second transistor 120 and the regulating transistors 130, 140 may comprise a source terminal 112, 122, 132, 142, a drain terminal 114, 124, 134, 144, and a gate terminal 116, 126, 136, 146. Voltage levels on the gate terminal control drain current of the transistors 110, 120, 130, 140.

The first transistor 110 and the second transistor 120 are arranged in a stacked connection with the drain terminal 114 of the first transistor 110 connected to the source terminal 122 of the second transistor 120. The source terminal 112 of the first transistor 110 may further be connected to ground and the drain terminal 124 of the second transistor 120 may be connected to a supply voltage (via the regulating transistors 130, 140).

The second transistor 120 and the first regulating transistor 130 are also arranged in a stacked connection with the drain terminal 124 of the second transistor 120 connected to the source terminal 132 of the first regulating transistor 130. The source terminal 122 of the second transistor 120 may further be connected to the drain terminal 114 of the first transistor 110 which is further connected to ground and the drain terminal 134 of the first regulating transistor 130 may be connected to the supply voltage (via the second regulating transistor 140 and possibly additional regulating transistors).

The first regulating transistor 130 and the second regulating transistor 140 are also arranged in a stacked connection with the drain terminal 134 of the first regulating transistor 130 connected to (possibly via additional regulating transistors) the source terminal 142 of the second regulating transistor 140. The source terminal 132 of the first regulating transistor 130 may further be connected to the drain terminal 124 of the second transistor 120 which is further connected to the first transistor 110 which is further connected to ground, and the drain terminal 144 of the second regulating transistor 140 may be connected to the supply voltage (possibly via additional regulating transistors).

The first transistor 110, the second transistor 120 and the regulating transistors 130, 140 being in a stacked connection implies that a current may flow between the supply voltage and ground through all transistors 110, 120, 130, 140.

The first transistor 110, the second transistor 120 and the regulating transistors 130, 140 may be implemented such that a gate leakage current of each transistor is negligible compared with a drain current. This implies that a current drawn from the supply voltage is flowing through all transistors 110, 120, 130, 140 equally, the current corresponding to the drain currents of the transistors 110, 120, 130, 140.

According to an embodiment, the first transistor 110 may be implemented with a thick gate oxide layer in order to ensure that gate leakage current is very low. Such transistors may be referred to as input/output transistors, as transistors used for communication with external devices often are implemented with a thick gate oxide layer. In particular, the oxide layer of the first transistor 110 may be thicker than the oxide layers of the second transistor 120 and the regulating transistors 130, 140 (which may be native transistors).

The voltage reference circuit 100 defines a first node 150 having a first voltage between the first transistor 110 and the second transistor 120. Since the first transistor 110 is arranged in a stacked connection with the second transistor 120, the drain terminal 114 of the first transistor 110 and the source terminal 122 of the second transistor 120 may be connected to the first node 150.

The first node 150 is further connected to the first regulating transistor 130 for feedback of the first voltage to the first regulating transistor 130. As shown in FIGS. 1-2, the gate terminal 136 of the first regulating transistor 130 may be connected to the first node 150. The first regulating transistor 130 is configured to provide a compensation for changes in the first voltage such that the voltage reference circuit 100 maintains a stable level of the first voltage.

The voltage reference circuit 100 defines a second node 152 having a second voltage between the second transistor 120 and the first regulating transistor 130. Since the second transistor 120 is arranged in a stacked connection with the first regulating transistor 130, the drain terminal 124 of the second transistor 120 and the source terminal 132 of the first regulating transistor 130 may be connected to the second node 152.

The second node 152 is further connected to the second regulating transistor 140 for feedback of the second voltage to the second regulating transistor 140. As shown in FIGS.

1-2, the gate terminal 146 of the second regulating transistor 140 may be connected to the second node 152. The second regulating transistor 140 is configured to provide a compensation for changes in the second voltage such that the voltage reference circuit 100 maintains a stable level of the second voltage.

The gate terminal 116 of the first transistor 110 is connected to the first node 150. Further, the gate terminal 126 of the second transistor 120 is connected to ground.

Neglecting channel length modulation and body effect, the first transistor 110 and the second transistor 120 have identical drain currents. The first transistor 110 and the second transistor 120 may form a two-transistor voltage reference circuit generating a first voltage at the first node 150 which may be used as a reference voltage.

The first regulating transistor 130 is added in a stacked connection with the second transistor 120. The gate terminal 136 of the first regulating transistor 130 is connected to the first node 150 receiving the first voltage at the gate terminal 136.

Any variation in the first voltage will thus be sensed by the gate terminal 136 of the first regulating transistor 130. Thanks to the regulating transistor 130, a stable first voltage level may be maintained. If a supply voltage fluctuates so that the first voltage level increases, an incremental change will be sensed by the change in the voltage at the gate terminal 136 of the first regulating transistor 130. This feedback forces voltage at the second node 152 to follow the voltage at the first node 150. When the first voltage level increases, the voltage at the second node 152 will push up potential at the source terminal 132 of the regulating transistor 130. This implies that the voltage between the supply voltage and the source terminal 132 of the regulating transistor 130 is reduced, and thereby a current from supply voltage to the second transistor 120 will be reduced such that the drain current of the second transistor 120 will degenerate and bring the reference voltage back to original value. If the reference voltage level instead decreases, the voltage reference circuit 100 operates vice versa to maintain the stable reference voltage level.

This implies that the first voltage level is insensitive to supply voltage variations and that the first regulating transistor 130 thus improves stability of the first voltage level. The first voltage at the first node 150 may be output as the reference voltage from the voltage reference circuit 100. However, the reference voltage may be generated in other nodes instead or several reference voltages of different magnitudes may be output by the voltage reference circuit 100.

All of the transistors 110, 120, 130, 140 may be configured to operate in saturation at a subthreshold region. Since the gate terminal 126 of the second transistor 120 is connected to ground and the source terminal is connected to the first node 150 providing the first voltage $V_{ref1}$, the gate-to-source voltage $V_{GS2}$ of the second transistor 120 is negative, $V_{GS2}=-V_{ref1}$.

The negative gate-to-source voltage $V_{GS2}$ implies that an extremely low drain current may be generated by the second transistor 120. The generated current is supplied to the first transistor 110 and the regulating transistors 130, 140.

An aspect ratio of the first regulating transistor 130 may equal an aspect ratio of the second transistor 120. As the second transistor 120 and the first regulating transistor 130 conduct the same drain current and have same physical dimensions (aspect ratio), the gate-to-source voltage $V_{GS2}$ of the second transistor 120 equals the gate-to-source voltage $V_{GS3}$ of the first regulating transistor 130, or in other words, the source-to-gate voltage $V_{SG2}$ of the second transistor 120 equals the source-to-gate voltage $V_{SG3}$ of the first regulating transistor 130. This implies that a voltage at the second node 152 is $V_{ref2}=V_{SG2}+V_{SG3}=2*V_{ref1}$.

Thus, by introducing the first regulating transistor 130, the insensitivity of the first voltage at the first node 150 to supply voltage variations is improved and also a voltage level at the first node 150 is scaled to a voltage level at the second node 152. Hence, the first regulating transistor 130 provides a first round of line regulation and scaling of reference voltage.

In a corresponding manner as described above, the second regulating transistor 140 is added in a stacked connection with the first regulating transistor 130. The gate terminal 146 of the second regulating transistor 140 is connected to the second node 152 receiving the second voltage at the gate terminal 146.

Thus, the second regulating transistor 140 may provide another round of line regulation, improving insensitivity of the second voltage at the second node 152 to supply voltage variations and further improving insensitivity of the first voltage at the first node 150 to supply voltage variations, and scaling, further providing a third voltage at a third node 154 between the first regulating transistor 130 and the second regulating transistor 140.

Since the first regulating transistor 130 is arranged in a stacked connection with the second regulating transistor 140, the drain terminal 134 of the first regulating transistor 130 and the source terminal 142 of the second regulating transistor 140 may be connected to the third node 154.

As shown in FIG. 2, the voltage reference circuit 100 may comprise only the first and the second regulating transistors 130, 140. In such case, the third voltage at the third node 154 is not provided to the gate terminal of any regulating transistor and the third voltage is not regulated. However, the third voltage is scaled in relation to the second voltage. If the aspect ratio of the second regulating transistor 140 equals the aspect ratio of the second transistor 120 and the aspect ratio of the first regulating transistor 130, a voltage at the third node 154 is $V_{ref3}=3*V_{ref1}$. However, the second regulating transistor 140 may be sized slightly differently to compensate for non-idealities in the voltage reference circuit 100.

The voltage reference circuit 100 may be configured to output any one of the first voltage at the first node 150, the second voltage at the second node 152 or the third voltage at the third node 154 as the reference voltage. The voltage reference circuit 100 may be set up differently in different use cases, such that the node from which the reference voltage is output may be selected in dependence on desired properties of the reference voltage. If a reference voltage having very low sensitivity to supply voltage variations is desired, the first voltage may be output as the reference voltage. If a reference voltage having low sensitivity to supply voltage variations and having a relatively high voltage level is desired, the second voltage may be output as the reference voltage. If a reference voltage having a high voltage level is desired, the third voltage may be output as the reference voltage.

It should further be realized that the voltage reference circuit 100 may be configured to output a plurality of reference voltages, which may be utilized in order to generate different voltage levels for biasing or supplying to an electronic circuit.

As shown in FIG. 1 and discussed above, the voltage reference circuit 100 may comprise additional regulating transistor(s) in addition to the first and second regulating transistors 130, 140. All of the regulating transistors 130, 140 may be arranged in a stack. Each regulating transistor 130, 140 may have its gate terminal 136, 146, connected to a node in the voltage reference circuit 100 providing regulation of a voltage level at the respective node. This implies that additional rounds of line regulation and scaling of the reference voltage may be provided.

A topmost regulating transistor in the stack is connected to supply voltage and a voltage at a node 158 between the topmost regulating transistor and the regulating transistor directly connected to the topmost regulating transistor may therefore not be regulated. This implies that although the node 158 has a highest voltage level, it may suffer from parameter variations, such as variations in supply voltage.

A node 156 which is connected to the gate terminal of the topmost regulating transistor is the node of the voltage reference circuit 100 having the largest voltage, which is also being regulated, by the topmost regulating transistor. Therefore, this node 156 may be of particular interest for use in output of the reference voltage and the voltage reference circuit 100 may use node 156 for output of the reference voltage.

Figure 3:
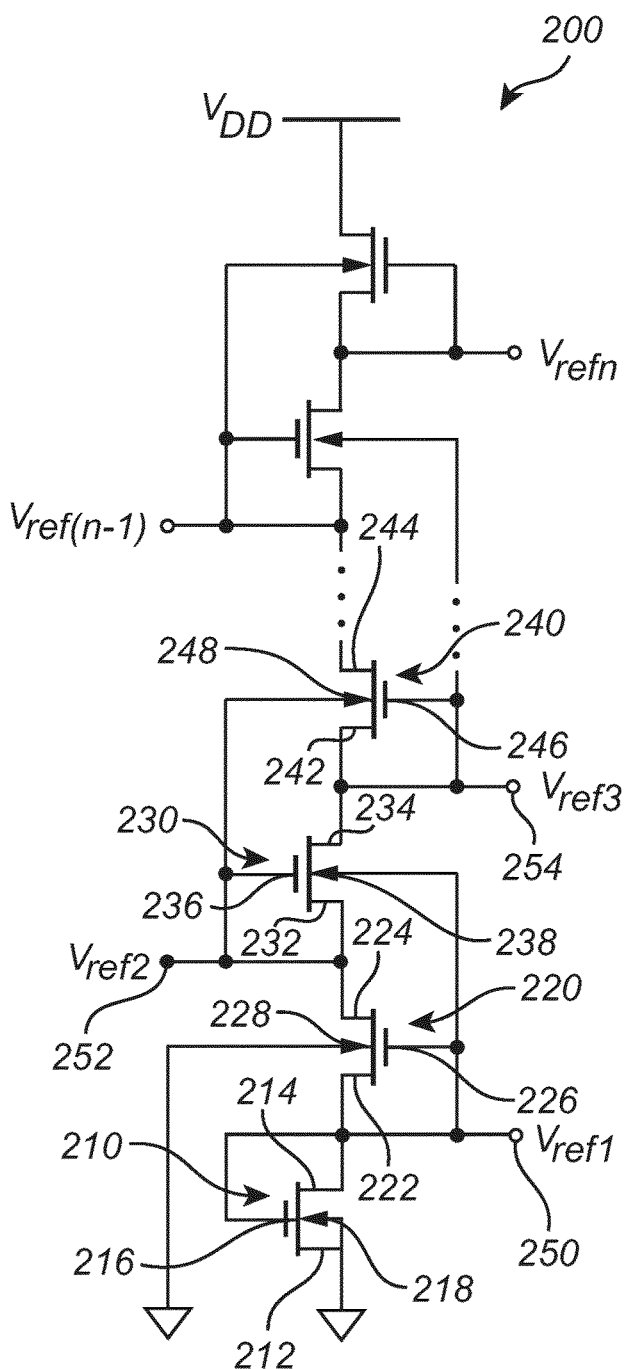
FIGS. 3-4 are schematic views of a voltage reference circuit according to a second embodiment.
Figure 4:
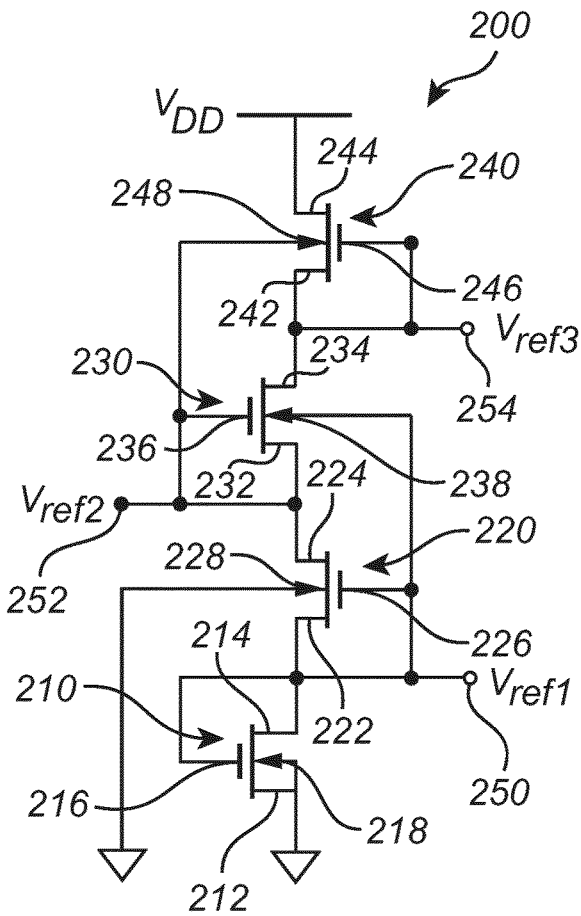

Referring now to FIGS. 3 and 4, a voltage reference circuit 200 according to a second embodiment will be described. The voltage reference circuit 200 comprises a first transistor 210, a second transistor 220 and at least a first regulating transistor 230 and a second regulating transistor 240. As illustrated in FIG. 3, the voltage reference circuit 200 may comprise a large number of regulating transistors and, as illustrated in FIG. 4, the voltage reference circuit 200 may comprise only the first regulating transistor 230 and the second regulating transistor 240.

Each of the first transistor 210, the second transistor 220 and the regulating transistors 230, 240 may be a nMOS transistor and the description below is based on the transistors being nMOS transistors. However, it should be realized that the first transistor 210 may instead be a pMOS transistor. In such case, source and drain terminals of the transistor should switch places with each other.

Each of the first transistor 210, the second transistor 220 and the regulating transistors 230, 240 may comprise a source terminal 212, 222, 232, 242, a drain terminal 214, 224, 234, 244, a gate terminal 216, 226, 236, 246 and a bulk terminal 218, 228, 238, 248. Voltage levels on the gate terminal and the bulk terminal control drain current of the transistors 210, 220, 230, 240. It should however be realized that the first transistor 210 need not necessarily be provided with a bulk terminal.

The voltage reference circuit 200 need not include native transistors, which implies that the voltage reference circuit 200 is available for technologies that do not support native transistors. However, the voltage reference circuit 200 instead utilizes bulk terminal of transistors.

Thus, the voltage reference circuit 200 may be particularly suited for implementation using technology for which bulk terminals are available. Hence, the voltage reference circuit 200 may for instance be formed using bulk complementary metal-oxide-semiconductor (CMOS) technology, wherein transistors for which a bulk terminal is needed are associated with deep n-wells. The voltage reference circuit 200 may alternatively be formed in fully-depleted silicon-on-insulator (FD-SOI) technology.

The first transistor 210 and the second transistor 220 are arranged in a stacked connection with the drain terminal 214 of the first transistor 210 connected to the source terminal 222 of the second transistor 220. The source terminal 212 of the first transistor 210 may further be connected to ground and the drain terminal 224 of the second transistor 220 may be connected to a supply voltage (via the regulating transistors 230, 240).

The second transistor 220 and the first regulating transistor 230 are also arranged in a stacked connection with the drain terminal 224 of the second transistor 220 connected to the source terminal 232 of the first regulating transistor 230. The source terminal 222 of the second transistor 220 may further be connected to the drain terminal 214 of the first transistor 210 which is further connected to ground and the drain terminal 234 of the first regulating transistor 230 may be connected to the supply voltage (via the second regulating transistor 240 and possibly additional regulating transistors).

The first regulating transistor 230 and the second regulating transistor 240 are also arranged in a stacked connection with the drain terminal 234 of the first regulating transistor 230 connected to (possibly via additional regulating transistors) the source terminal 242 of the second regulating transistor 240. The source terminal 232 of the first regulating transistor 230 may further be connected to drain terminal 224 of the second transistor 220 which is further connected to the first transistor 210 which is further connected to ground, and the drain terminal 244 of the second regulating transistor 240 may be connected to the supply voltage (possibly via additional regulating transistors).

The first transistor 210, the second transistor 220 and the regulating transistors 230, 240 being in a stacked connection implies that a current may flow between the supply voltage and ground through all transistors 210, 220, 230, 240.

The first transistor 210, the second transistor 220 and the regulating transistors 230, 240 may be implemented such that a gate leakage current of each transistor is negligible compared with a drain current. This implies that a current drawn from the supply voltage is flowing through all transistors 210, 220, 230, 240 equally, the current corresponding to the drain currents of the transistors 210, 220, 230, 240.

According to an embodiment, all of the transistor 210, 220, 230, 240 may be implemented with a thick gate oxide layer in order to ensure that gate leakage current is very low. Such transistors may be referred to as input/output transistors, as transistors used for communication with external devices often are implemented with a thick gate oxide layer. The second transistor 220 and the regulating transistors 230, 240 may be configured with a lower threshold voltage than the first transistor 210.

The voltage reference circuit 200 defines a first node 250 having a first voltage between the first transistor 210 and the second transistor 220. Since the first transistor 210 is arranged in a stacked connection with the second transistor 220, the drain terminal 214 of the first transistor 210 and the source terminal 222 of the second transistor 220 may be connected to the first node 250.

The first node 250 is further connected to the first regulating transistor 230 for feedback of the first voltage to the first regulating transistor 230. As shown in FIGS. 3-4, the bulk terminal 238 of the first regulating transistor 230 may be connected to the first node 250. The first regulating transistor 230 is configured to provide a compensation for changes in the first voltage such that the voltage reference circuit 200 maintains a stable level of the first voltage.

The voltage reference circuit 200 defines a second node 252 having a second voltage between the second transistor 220 and the first regulating transistor 230. Since the second transistor 220 is arranged in a stacked connection with the first regulating transistor 230, the drain terminal 224 of the second transistor 220 and the source terminal 232 of the first regulating transistor 230 may be connected to the second node 252.

The second node 252 is further connected to the second regulating transistor 240 for feedback of the second voltage to the second regulating transistor 240. As shown in FIGS. 3-4, the bulk terminal 248 of the second regulating transistor 240 may be connected to the second node 252. The second regulating transistor 240 is configured to provide a compensation for changes in the second voltage such that the voltage reference circuit 200 maintains a stable level of the second voltage.

The gate terminal 216 of the first transistor 210 is connected to the drain terminal 214 of the first transistor 210 and to the first node 250. The bulk terminal 218 of the first transistor 210 is connected to the source terminal 212 of the first transistor 210 and connected to ground. Thus, the first transistor 210 may be said to be diode-connected.

The second transistor 220 may be configured to generate current in the voltage reference circuit 200. The gate terminal 226 and the source terminal 222 of the second transistor 220 are connected to each other, which also implies that the gate terminal 226 is connected to the first node 250. Since the gate terminal 226 and the source terminal 222 are connected, the second transistor 220 has a zero gate-to-source voltage $V_{GS2}$. The bulk terminal 228 of the second transistor 220 may be connected to ground.

The second transistor 220 may be configured to operate in saturation at a subthreshold region of the second transistor 220. If a drain-to-source voltage $V_{DS2}$ of the second transistor 220 is larger than $4*V_T$ (where $V_T$ is thermal voltage), drain current of the second transistor 220 is controlled only by the bulk-to-source voltage $V_{BS2}$ of the second transistor 220. Since the bulk terminal 228 of the second transistor 220 is connected to ground, the bulk-to-source voltage $V_{BS2}$ of the second transistor 220 is negative. Further, the source terminal 222 of the second transistor 220 is connected to the first node 250 providing the reference voltage $V_{ref1}$, such that $V_{BS2}=-V_{ref1}$.

The zero gate-to-source voltage $V_{GS2}$ and the negative bulk-to-source voltage $V_{BS2}$ implies that an extremely low drain current $I_{D2}$ may be generated by the second transistor 220. The generated current is supplied to the diode-connected first transistor 210.

Since the gate-to-source voltage $V_{GS2}$ of the second transistor 220 is always zero and the bulk-to-source voltage $V_{BS2}$ is constant (as the output reference voltage $V_{ref1}$ is constant in the voltage reference circuit 200 and $V_{BS2}=-V_{ref1}$), the drain current $I_{D2}$ will be constant if drain-to-source voltage $V_{DS2}$ of the second transistor 220 is constant.

As will be shown below, by adding the first regulating transistor 230, the drain-to-source voltage $V_{DS2}$ of the second transistor 220 may be maintained constant.

The drain current of the first regulating transistor 230 equals the drain current of the second transistor 220. The gate terminal 236 of the first regulating transistor 230 may be connected to the source terminal 232 of the first regulating transistor 230. This implies that the gate-to-source voltage $V_{GS3}$ of the first regulating transistor 230 is zero. Hence, the drain current through the first regulating transistor 230 is controlled by the bulk-to-source voltage $V_{BS3}$.

An aspect ratio of the first regulating transistor 230 may equal an aspect ratio of the second transistor 220. This implies that, with the regulating transistor 230 and the second transistor 220 conducting the same current, the bulk-to-source voltage $V_{BS3}$ of the regulating transistor 230 equals the bulk-to-source voltage $V_{BS2}$ of the second transistor 220, i.e., $V_{BS3}=V_{BS2}=V_{ref1}$. Hence, using the same aspect ratio for the regulating transistor 230 and the second transistor 220 provides an accurate control of the first voltage at the first node 250.

The bulk terminal 238 of the first regulating transistor 230 is connected to the first node 250 and, hence, also connected to the source terminal 222 of the second transistor 220. The source terminal 232 of the first regulating transistor 230 is connected to the drain terminal 224 of the second transistor 220. This implies that the drain-to-source voltage $V_{DS2}$ of the second transistor 220 is regulated by the condition $V_{DS2}=-V_{BS3}=V_{ref1}$.

Thanks to the first regulating transistor 230, a stable first voltage level may be maintained. If a supply voltage fluctuates so that the reference voltage level increases, an incremental change will be sensed by the change in the bulk-to-source voltage $V_{BS3}$ of the first regulating transistor 230. This feedback forces voltage at the second node 252 to follow the voltage at the first node 250. When the first voltage level increases, the voltage at the second node 252 will push up potential at the source terminal 232 of the regulating transistor 230. This implies that the voltage between the supply voltage and the source terminal 232 of the regulating transistor 230 is reduced, and thereby a current from supply voltage to the second transistor 220 will be reduced such that the drain current of the second transistor 220 will degenerate and bring the reference voltage back to original value. If the reference voltage level instead decreases, the voltage reference circuit 200 operates vice versa to maintain the stable first voltage level.

This implies that the first voltage level is insensitive to supply voltage variations and that the first regulating transistor 230 thus improves stability of the first voltage level. The first voltage at the first node 250 may be output as the reference voltage from the voltage reference circuit 200. However, the reference voltage may be generated in other nodes instead or several reference voltages of different magnitudes may be output by the voltage reference circuit 200.

As the second transistor 220 and the first regulating transistor 230 conduct the same drain current and have same physical dimensions (aspect ratio), the bulk-to-source voltage $V_{BS2}$ of the second transistor 220 equals the bulk-to-source voltage $V_{BS3}$ of the first regulating transistor 230, or in other words, the source-to-bulk voltage $V_{SB2}$ of the second transistor 220 equals the source-to-bulk voltage $V_{SB3}$ of the first regulating transistor 230. This implies that a voltage at the second node 252 is $V_{ref2}=2*V_{ref1}$.

Thus, by introducing the first regulating transistor 230, the insensitivity of the first voltage at the first node 250 to supply voltage variations is improved and also a voltage level at the first node 250 is scaled to a voltage level at the second node 252. Hence, the first regulating transistor 230 provides a first round of line regulation and scaling of reference voltage.

In a corresponding manner as described above, the second regulating transistor 240 is added in a stacked connection with the first regulating transistor 230. The bulk terminal 248 of the second regulating transistor 240 is connected to the second node 252 receiving the second voltage at the bulk terminal 248. Further, the gate terminal 246 of the second regulating transistor 240 is connected to the source terminal 242 of the second regulating transistor 240 such that the gate-to-source voltage is zero and that the drain current through the second regulating transistor 240 is controlled by the bulk-to-source voltage.

Thus, the second regulating transistor 240 may provide another round of line regulation, improving insensitivity of the second voltage at the second node 252 to supply voltage variations and further improving insensitivity of the first voltage at the first node 250 to supply voltage variations, and scaling, further providing a third voltage at a third node 254 between the first regulating transistor 230 and the second regulating transistor 240.

Since the first regulating transistor 230 is arranged in a stacked connection with the second regulating transistor 240, the drain terminal 234 of the first regulating transistor 230 and the source terminal 242 of the second regulating transistor 240 may be connected to the third node 254.

As shown in FIG. 4, the voltage reference circuit 200 may comprise only the first and the second regulating transistors 230, 240. In such case, the third voltage at the third node 254 is not provided to the bulk terminal of any regulating transistor and the third voltage is not regulated. However, the third voltage is scaled in relation to the second voltage. If the aspect ratio of the second regulating transistor 240 equals the aspect ratio of the second transistor 220 and the aspect ratio of the first regulating transistor 230, a voltage at the third node 254 is $V_{ref3}=3*V_{ref1}$. However, the second regulating transistor 240 may be sized slightly differently to compensate for non-idealities in the voltage reference circuit 200.

As explained above in relation to the voltage reference circuit 100, the voltage reference circuit 200 may be configured to output any one of or a plurality of the first voltage at the first node 250, the second voltage at the second node 252 or the third voltage at the third node 254 as the reference voltage.

As shown in FIG. 3 and discussed above, the voltage reference circuit 200 may comprise additional regulating transistor(s) in addition to the first and second regulating transistors 230, 240. All of the regulating transistors 230, 240 may be arranged in a stack. Each regulating transistor 230, 240 may have its bulk terminal 238, 248, connected to a node in the voltage reference circuit 200 providing regulation of a voltage level at the respective node. This implies that additional rounds of line regulation and scaling of the reference voltage may be provided.

By connecting the first and second nodes to bulk terminals 238, 248 of the first and second regulating transistors 230, 240, respectively, body effect of the regulating transistors 230, 240 is utilized for maintaining stable voltage levels. This implies that, in comparison to the voltage reference circuit 100 illustrated in FIGS. 1-2, losses due to body effects in scaling of the voltage between different nodes may be avoided.

The voltage reference circuits 100, 200 illustrated in FIGS. 2 and 4 have been simulated to analyze properties of the voltage reference circuits.

The simulations have been based on the following parameters of the transistors:

The voltage reference circuits 100, 200 are simulated using 55 nm bulk CMOS technology. In voltage reference circuit 100, the first transistor 110 is an input/output transistor with a channel width of 10 μm, a channel length of 10 μm and a threshold voltage of 594 mV. The second transistor 120 and the regulating transistors 130, 140 are native transistors with a channel width of 1 μm, a channel length of 10 μm, and a threshold voltage of –25 mV. In voltage reference circuit 200, the first transistor 210 is an input/output transistor with a channel width of 4 μm, a channel length of 12 μm, and a threshold voltage of 594 mV. The second transistor 220 and the regulating transistors 230, 240 are transistors associated with deep n-well with a channel width of 12 μm, a channel length of 12 μm, and a threshold voltage of 279 mV.

Figure 5A:
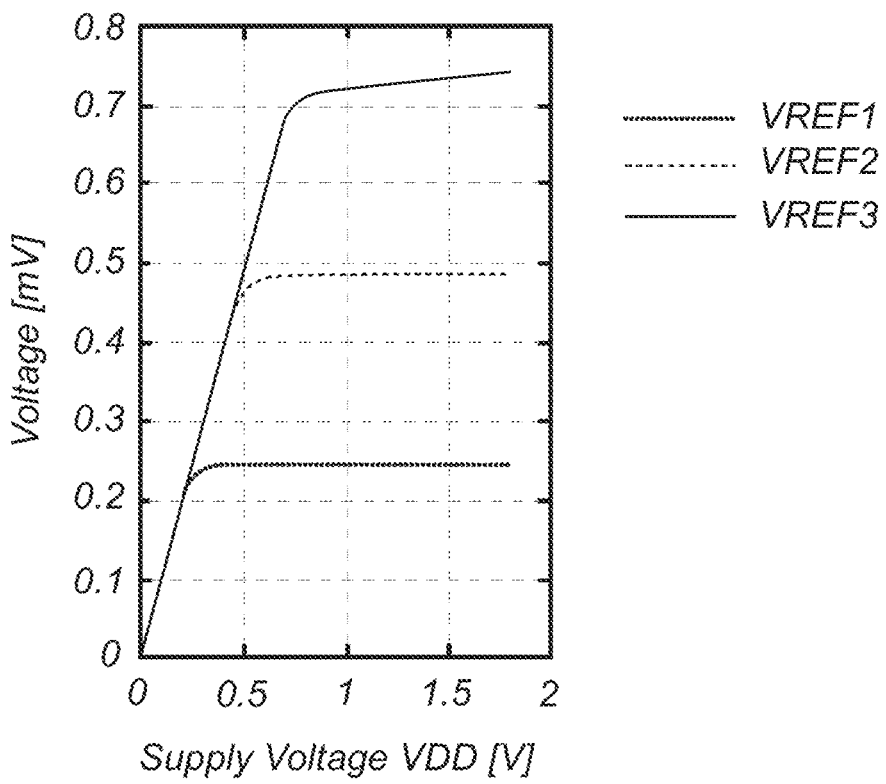
FIGS. 5a-5b are graphs illustrating reference voltage output by the voltage reference circuits of FIG. 2 and FIG. 4, respectively, in dependence of variation of supply voltage.
Figure 5B:
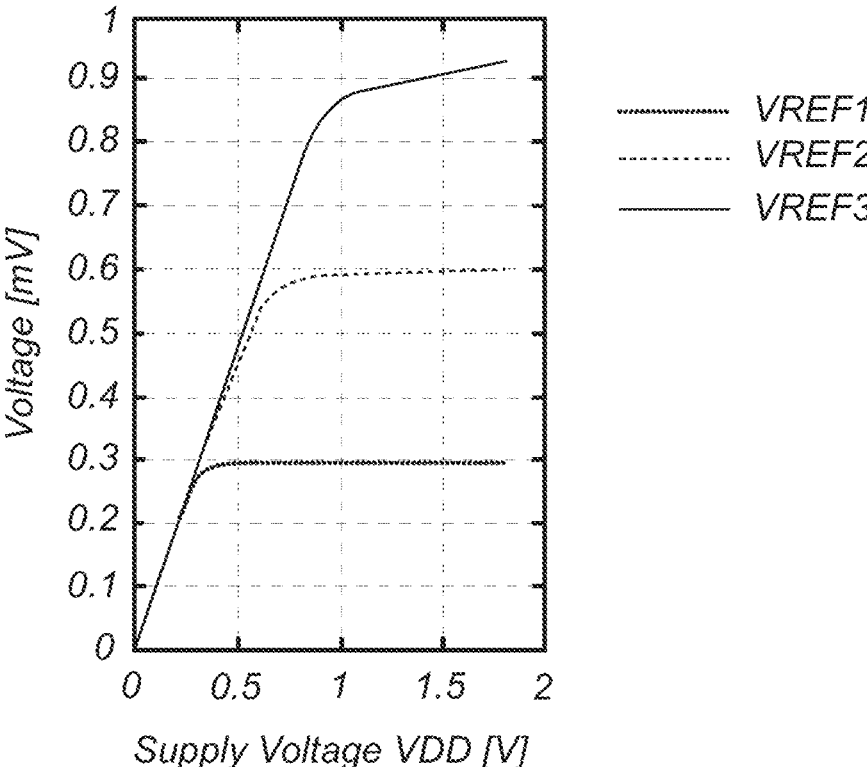

Referring now to FIGS. 5a-5b, a sensitivity of the voltage reference circuits 100, 200 to variations in supply voltage from 0-1.8 V is illustrated. In FIG. 5a, the reference voltage at each of the first node 150, the second node 152, and the third node 154 for the voltage reference circuit 100 of FIG. 2 is illustrated. In FIG. 5b, the reference voltage at each of the first node 250, the second node 252, and the third node 254 for the voltage reference circuit 200 of FIG. 4 is illustrated. As can be seen from FIGS. 5a-5b, the second voltage $V_{ref2}$ is approximately two times the first voltage $V_{ref1}$ and the third voltage $V_{ref3}$ is approximately three times the first voltage $V_{ref1}$.

FIGS. 5a-5b further illustrate that the voltage level of the first voltage and the second voltage is insensitive to variations in supply voltage, whereas the voltage level of the third voltage (which is not regulated) exhibits some dependency on the supply voltage. The first voltage $V_{ref1}$ is least sensitive to variations in supply voltage providing a good line sensitivity (LS) (percentage of change in output reference voltage in dependence of change in supply voltage). For the voltage reference circuit 100, the first voltage exhibits an LS of 0.01% N in a range of supply voltage from 0.9-1.1 V. For the voltage reference circuit 200, the first voltage exhibits an LS of 0.033% N in a range of supply voltage from 0.9-1.1 V. It may be noted that the voltage reference circuit 200 provides a higher value of the reference voltage, whereas the voltage reference circuit 100 provides a lower LS.

For the voltage reference circuit 100, the third voltage exhibits an LS of 3.8% N in a range of supply voltage from 0.9-1.1 V. For the voltage reference circuit 200, the third voltage exhibits an LS of 8.6% N in a range of supply voltage from 0.9-1.1 V. The third voltage is not regulated and therefore exhibits a sensitivity to supply voltage variations.

Figure 6A:
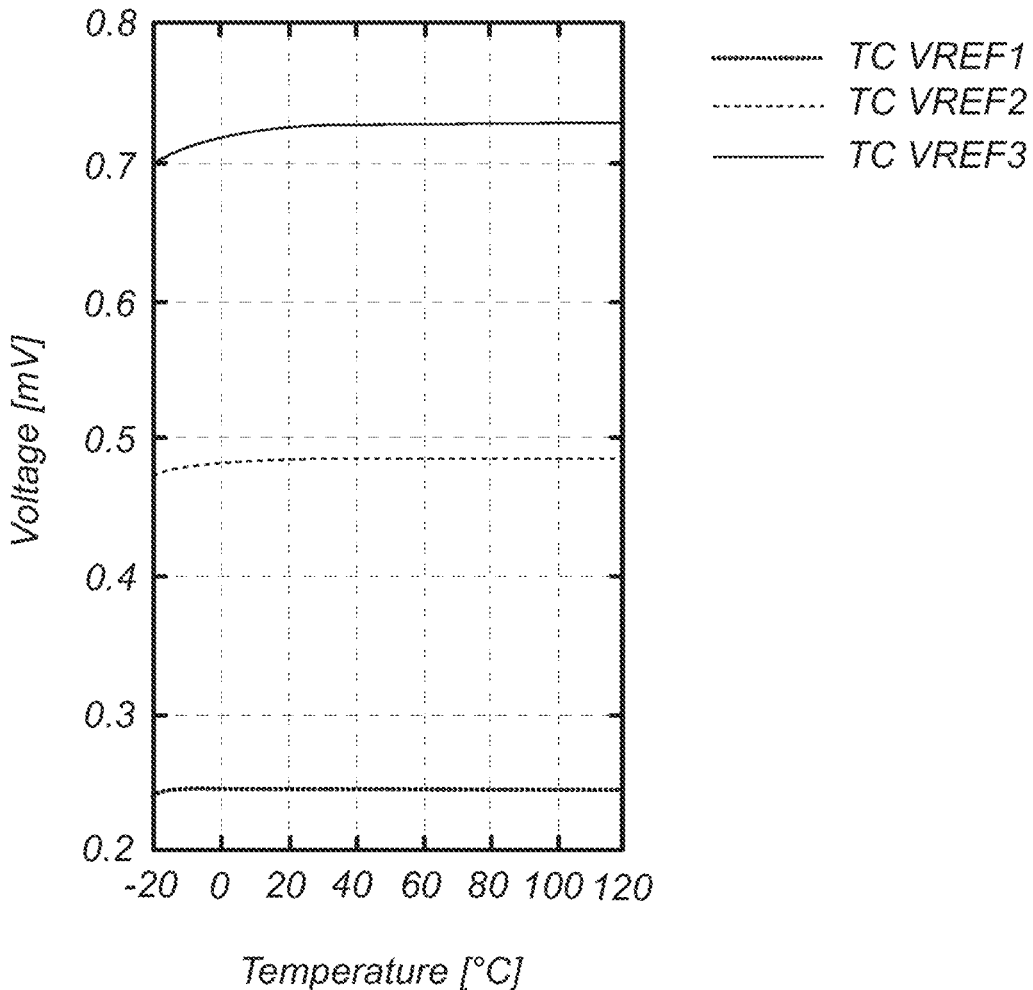
FIGS. 6a-6b are graphs illustrating reference voltage output by the voltage reference circuits of FIG. 2 and FIG. 4, respectively, in dependence of variation of temperature.
Figure 6B:
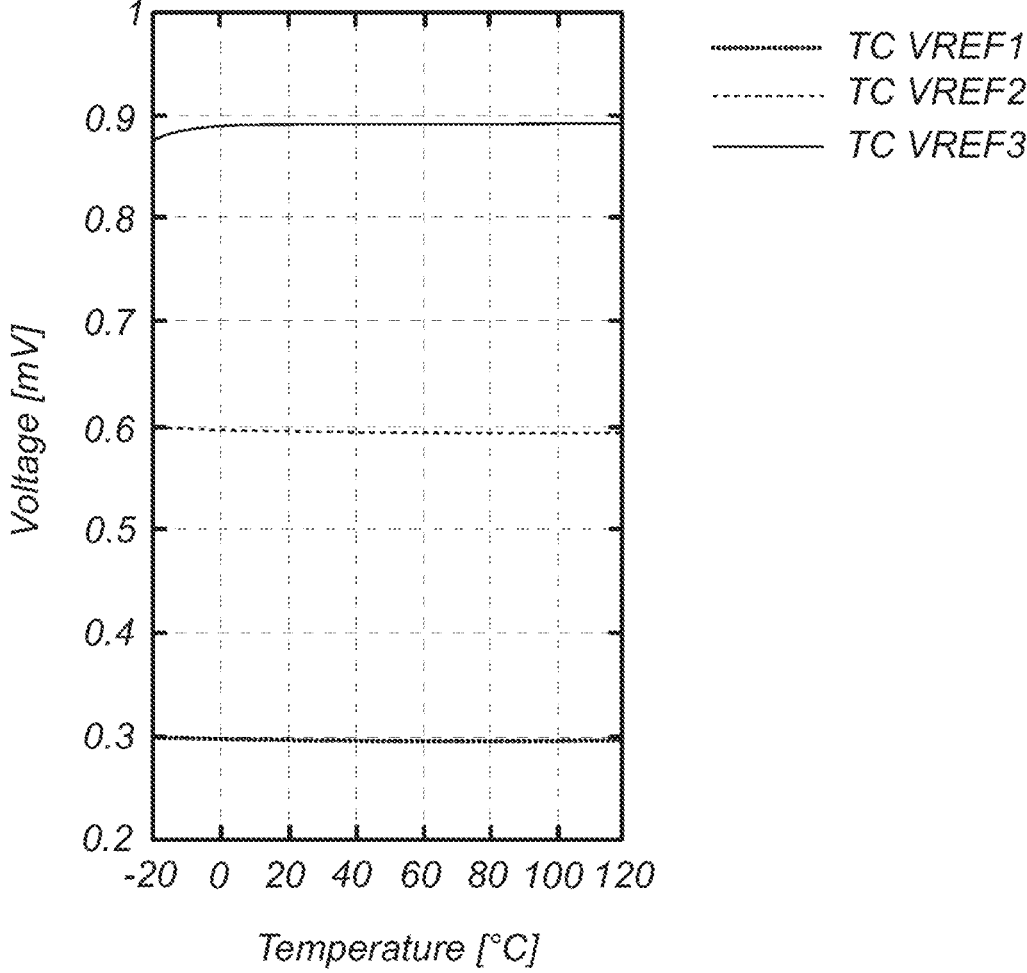

Referring now to FIGS. 6a-6b, temperature characteristics of the reference voltage of the first voltage, the second voltage, and the third voltage output by the voltage reference circuit 100 (FIG. 6a) and the voltage reference circuit 200 (FIG. 6b) are illustrated.

As is shown in FIGS. 6a-6b, the reference voltage output by the voltage reference circuits 100, 200 is stable between –20° C. to 120° C. Within this temperature range, a temperature coefficient (TC) (variation of the output reference voltage as a function of temperature) of the reference voltages is 49.6 ppm, 173.5 ppm, and 289.2 ppm for the first voltage, the second voltage, and the third voltage, respectively, for the voltage reference circuit 100. Further, within the temperature range, the TC of the reference voltages is 70.3 ppm, 43.7 ppm, and 118.9 ppm for the first voltage, the second voltage, and the third voltage, respectively, for the voltage reference circuit 200.

Figure 7:
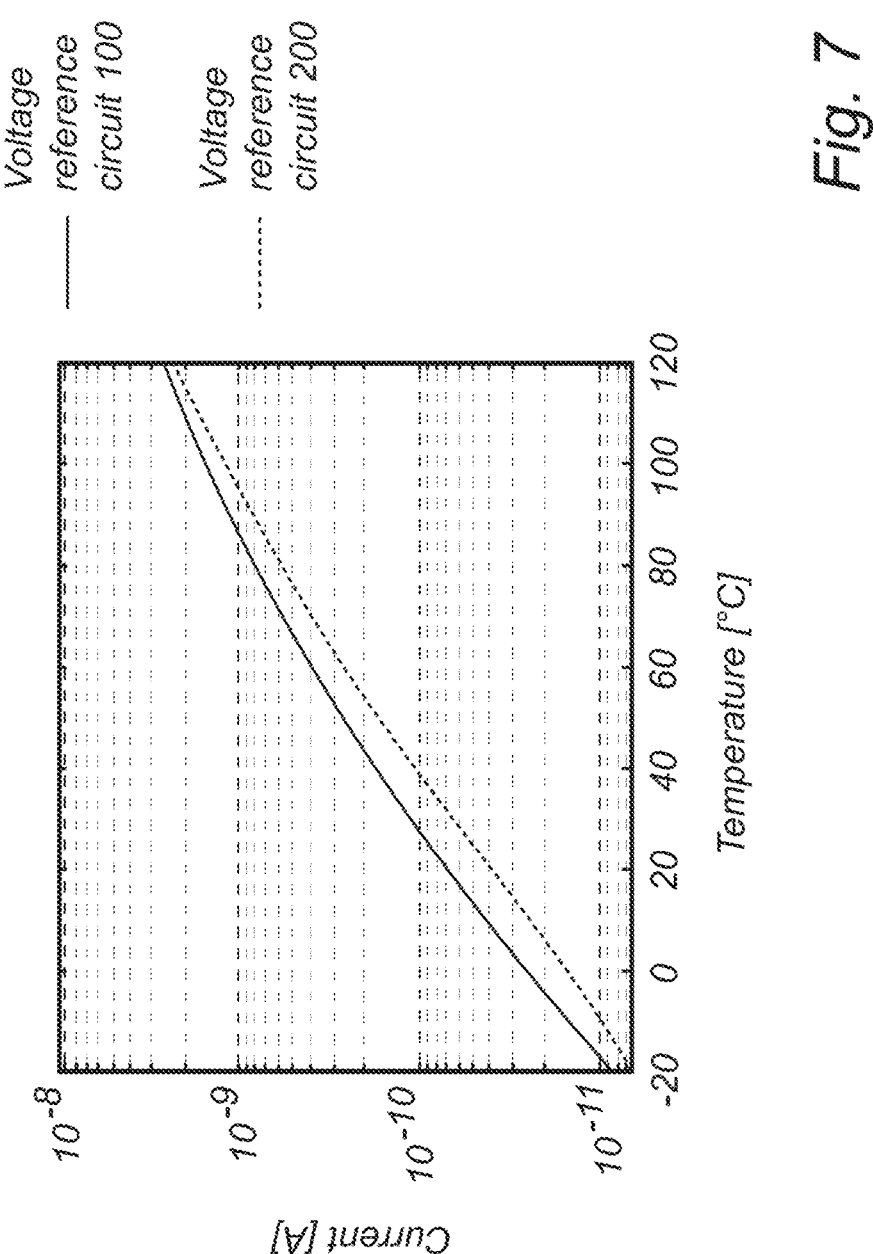
FIG. 7 is a graph illustrating a current consumed by the voltage reference circuits of FIG. 2 and FIG. 4, respectively, in dependence of variation in temperature.

Referring now to FIG. 7, current consumption of the voltage reference circuits 100, 200 is illustrated as a function of temperature, while keeping a supply voltage constant at 1.2 V. As can be seen, currents consumed by the voltage reference circuits 100, 200 increases almost exponentially over the temperature. The voltage reference circuit 200 consumes a higher current than the voltage reference circuit 100 for the entire temperature range. At room temperature, the voltage reference circuit 100 consumes 51 pA and the voltage reference circuit 200 consumes 89 pA.

Figure 8:
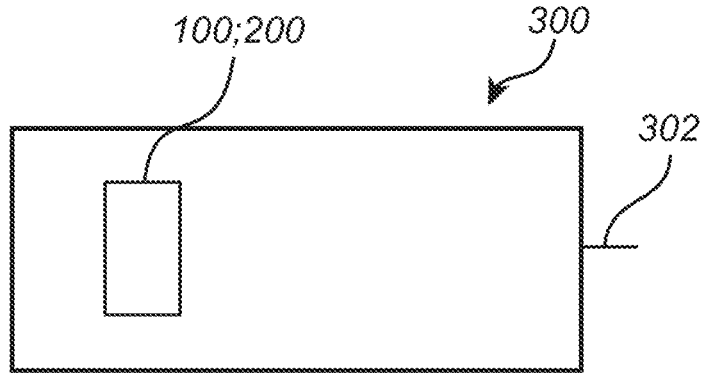
FIG. 8 is a schematic view of a power management unit according to an embodiment.

It should be realized that the voltage reference circuits 100, 200 may be used in any type of circuit or device where a stable voltage reference is desired. For instance, as shown in FIG. 8, a power management unit 300 may comprise any of the voltage reference circuits 100, 200 described above.

The power management unit 300 may be configured to control power functions of modules in electronic devices. Thus, the power management unit 300 may control whether modules are active or in sleep mode and may control power to modules.

The power management unit 300 may be configured to provide a DC voltage to modules of an electronic device, such as to integrated circuits. Thus, the power management unit 300 may need to ensure that a stable voltage level of the DC voltage is provided. In this regard, the power management unit 300 may be configured to produce the DC voltage based on a reference voltage output by the voltage reference circuit 100, 200 at a suitable node of the voltage reference circuit 100, 200 depending on the level of the DC voltage to be produced by the power management unit 300.

The power management unit 300 may comprise an output interface 302 for communicating with modules of the electronic device. The power management unit 300 may thus send signals for controlling functionality of the modules and may also supply a DC voltage to the modules over the output interface 302.

Since the power management unit 300 controls whether modules are active or in a sleep mode, the power management unit 300 may be maintained active when turning off the electronic device in which the power management unit 300 is arranged. Thus, power consumption of the power management unit 300 is important, in particular, if the power management unit 300 is arranged in a battery-powered device which may be awake only for a fraction of time, which may be the case for IoT-devices.

The voltage reference circuit 100, 200 consumes very small power, as discussed above. Hence, the voltage reference circuits 100, 200 are suited for being used in the power management unit 300.

Figure 9:
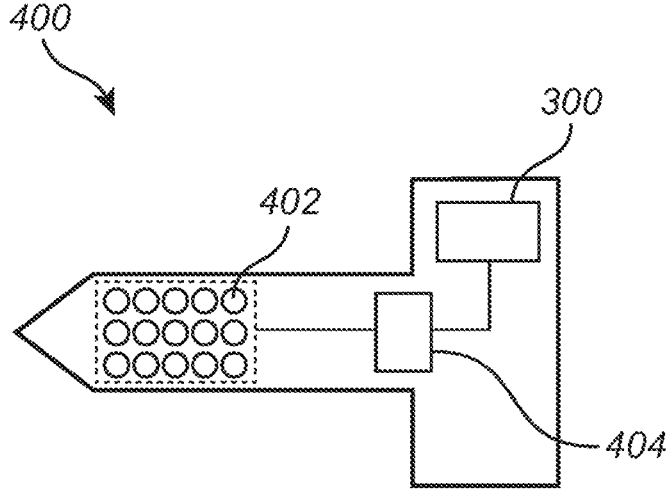
FIG. 9 is a schematic view of a neural sensing apparatus according to an embodiment.

Referring now to FIG. 9, a neural sensing apparatus 400 according to an embodiment will be described.

The neural sensing apparatus 400 may be in form of a neural probe which may be at least partly inserted into a brain. The neural sensing apparatus 400 may comprise electrodes 402 for neural sensing and readout circuitry 404 for reading out signals from the electrodes 402.

The neural sensing apparatus 400 may comprise the power management unit 300 for power management of the neural sensing apparatus 400. The power management unit 300 may be configured to control whether modules, such as the readout circuitry 404, of the neural sensing apparatus 400 are active or in a sleep mode.

The power management unit 300 may further comprise any of the voltage reference circuits 100, 200. The power consumption of the power management unit 300 of the neural sensing apparatus 400 may be very low thanks to the power management unit 300 which utilizes a voltage reference circuit 100, 200 which consumes very small power, as discussed above.

The power management unit 300 may be configured to produce a DC voltage at a voltage level suitable for the neural sensing apparatus 400 thanks to capability of scaling reference voltage output by the voltage reference circuit 100, 200.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A voltage reference circuit comprising:
a first transistor comprising a gate terminal, a source terminal, and a drain terminal;
a second transistor comprising a gate terminal, a source terminal, and a drain terminal, wherein the first transistor and the second transistor are arranged in a stacked connection between a terminal connected to ground and a terminal connected to a supply voltage, wherein a first voltage is provided at a first node between the first transistor and the second transistor;
a first regulating transistor comprising a gate terminal, a source terminal, and a drain terminal, wherein the first regulating transistor is connected between the supply voltage and the first transistor in a stacked connection with the second transistor, wherein a second voltage is provided at a second node between the second transistor and the first regulating transistor, and wherein the first regulating transistor is connected to the first node for compensating changes in the first voltage at the first node to maintain a stable first voltage level;
a second regulating transistor comprising a gate terminal, a source terminal, and a drain terminal, wherein the second regulating transistor is connected between the supply voltage and the second transistor in a stacked connection with the first regulating transistor, wherein a third voltage is provided at a third node between the first regulating transistor and the second regulating transistor, and wherein the second regulating transistor is connected to the second node for compensating changes in the second voltage at the second node to maintain a stable second voltage level,
wherein the voltage reference circuit is configured to output at least one of the first voltage, the second voltage, or the third voltage as a reference voltage; and
at least one additional regulating transistor, wherein the first regulating transistor, the second regulating transistor and the at least one additional regulating transistor form a stack between the supply voltage and the second transistor, wherein an additional node is provided between each pair of regulating transistors in the stack and the additional node is connected to a regulating transistor immediately above the pair of regulating transistors in the stack for compensating changes in the voltage at the additional node.

2. The voltage reference circuit according to claim 1, wherein the first transistor, the second transistor, the first regulating transistor, and the second regulating transistor are all n-type metal-oxide-semiconductor, nMOS, transistors, and wherein a drain terminal of the first transistor is connected to a source terminal of the second transistor, a drain terminal of the second transistor is connected to a source terminal of the first regulating transistor and a drain terminal of the first regulating transistor is connected to a source terminal of the second regulating transistor, and wherein the first node is connected to the drain terminal of the first transistor and the source terminal of the second transistor, the second node is connected to the drain terminal of the second transistor and the source terminal of the first regulating transistor, and the third node is connected to the drain terminal of the first regulating transistor and the source terminal of the second regulating transistor.

3. The voltage reference circuit according to claim 1, wherein an aspect ratio of the first regulating transistor equals an aspect ratio of the second transistor.

4. The voltage reference circuit according to claim 1, wherein the voltage reference circuit is configured to output a reference voltage from a node having a largest voltage and being regulated by a regulating transistor.

5. The voltage reference circuit according to claim 1, wherein the voltage reference circuit is configured to output more than one reference voltage.

6. The voltage reference circuit according to claim 1, wherein each of the first transistor, the second transistor, the first regulating transistor and the second regulating transistor further comprises a bulk terminal, and wherein the first node is connected to the bulk terminal of the first regulating transistor, and the second node is connected to the bulk terminal of the second regulating transistor.

7. The voltage reference circuit according to claim 6, wherein the gate terminal of the second transistor is connected to the source terminal of the second transistor, the gate terminal of the first regulating transistor is connected to the source terminal of the first regulating transistor and the gate terminal of the second regulating transistor is connected to the source terminal of the second regulating transistor.

8. The voltage reference circuit according to claim 6, wherein the bulk terminal of the first transistor is connected to ground and wherein the bulk terminal of the second transistor is connected to ground.

9. The voltage reference circuit according to claim 6, wherein the first transistor, the second transistor, the first regulating transistor and the second regulating transistor are input/output transistors.

10. The voltage reference circuit according to claim 1, wherein the first node is connected to the gate terminal of the first regulating transistor, and the second node is connected to the gate terminal of the second regulating transistor.

11. The voltage reference circuit according to claim 10, wherein the gate terminal of the second transistor is connected to ground.

12. The voltage reference circuit according to claim 10, wherein the first transistor is an input/output transistor and wherein each of the second transistor, the first regulating transistor and the second regulating transistor is a native transistor, an oxide layer of the native transistor being thinner than an oxide layer of the input/output transistor.

13. The voltage reference circuit according to claim 1, wherein the first transistor, the second transistor, the first regulating transistor and the second regulating transistor are all configured to operate at a subthreshold region.

14. The voltage reference circuit according to claim 1, wherein the gate terminal of the first transistor is connected to the first node.

15. A power management unit comprising the voltage reference circuit according to claim 1, the power management unit being configured to produce a direct current, DC, voltage based on the reference voltage.

16. A neural sensing apparatus comprising the power management unit according to claim 15.

17. A voltage reference circuit comprising:
a first transistor comprising a gate terminal, a source terminal, and a drain terminal;
a second transistor comprising a gate terminal, a source terminal, and a drain terminal, wherein the first transistor and the second transistor are arranged in a stacked connection between a terminal connected to ground and a terminal connected to a supply voltage, wherein a first voltage is provided at a first node between the first transistor and the second transistor;
a first regulating transistor comprising a gate terminal, a source terminal, and a drain terminal, wherein the first regulating transistor is connected between the supply voltage and the first transistor in a stacked connection with the second transistor, wherein a second voltage is provided at a second node between the second transistor and the first regulating transistor, and wherein the first regulating transistor is connected to the first node for compensating changes in the first voltage at the first node to maintain a stable first voltage level; and
a second regulating transistor comprising a gate terminal, a source terminal, and a drain terminal, wherein the second regulating transistor is connected between the supply voltage and the second transistor in a stacked connection with the first regulating transistor, wherein a third voltage is provided at a third node between the first regulating transistor and the second regulating transistor, and wherein the second regulating transistor is connected to the second node for compensating changes in the second voltage at the second node to maintain a stable second voltage level,
wherein the voltage reference circuit is configured to output at least one of the first voltage, the second voltage, or the third voltage as a reference voltage, and
wherein the first transistor, the second transistor, the first regulating transistor, and the second regulating transistor are all n-type metal-oxide-semiconductor, nMOS, transistors, and wherein a drain terminal of the first transistor is connected to a source terminal of the second transistor, a drain terminal of the second transistor is connected to a source terminal of the first regulating transistor and a drain terminal of the first regulating transistor is connected to a source terminal of the second regulating transistor, and wherein the first node is connected to the drain terminal of the first transistor and the source terminal of the second transistor, the second node is connected to the drain terminal of the second transistor and the source terminal of the first regulating transistor, and the third node is connected to the drain terminal of the first regulating transistor and the source terminal of the second regulating transistor.

18. A voltage reference circuit comprising:
a first transistor comprising a gate terminal, a source terminal, and a drain terminal;
a second transistor comprising a gate terminal, a source terminal, and a drain terminal, wherein the first transistor and the second transistor are arranged in a stacked connection between a terminal connected to ground and a terminal connected to a supply voltage, wherein a first voltage is provided at a first node between the first transistor and the second transistor;
a first regulating transistor comprising a gate terminal, a source terminal, and a drain terminal, wherein the first regulating transistor is connected between the supply voltage and the first transistor in a stacked connection with the second transistor, wherein a second voltage is provided at a second node between the second transistor and the first regulating transistor, and wherein the first regulating transistor is connected to the first node for compensating changes in the first voltage at the first node to maintain a stable first voltage level;
a second regulating transistor comprising a gate terminal, a source terminal, and a drain terminal, wherein the second regulating transistor is connected between the supply voltage and the second transistor in a stacked connection with the first regulating transistor, wherein a third voltage is provided at a third node between the first regulating transistor and the second regulating transistor, and wherein the second regulating transistor is connected to the second node for compensating changes in the second voltage at the second node to maintain a stable second voltage level;

wherein the voltage reference circuit is configured to output at least one of the first voltage, the second voltage, or the third voltage as a reference voltage; and wherein the gate terminal of the first transistor is connected to the first node.

* * * * *